United States Patent [19]

Odenwälder et al.

[11] 4,186,012
[45] Jan. 29, 1980

[54] LIGHT SENSITIVE COLOR PHOTOGRAPHIC MATERIAL CONTAINING DEVELOPMENT INHIBITOR RELEASING COUPLER

[75] Inventors: Heinrich Odenwälder, Cologne; Walter Puschel, Leverkusen, both of Fed. Rep. of Germany; Robert J. Pollet, Berchem, Belgium; Erwin Ranz, Leverkusen, Fed. Rep. of Germany

[73] Assignee: Agfa-Gevaert Aktiengesellschaft, Fed. Rep. of Germany

[21] Appl. No.: 882,631

[22] Filed: Mar. 2, 1978

[30] Foreign Application Priority Data

Apr. 5, 1977 [DE] Fed. Rep. of Germany ....... 2709688

[51] Int. Cl.$^2$ .................... G03C 1/48; G03C 1/06; G03C 1/40; G03C 5/30
[52] U.S. Cl. .................................... 430/544; 430/957; 430/379; 430/382; 430/218
[58] Field of Search ............... 96/76 R, 77, 95, 100, 96/56, 9, 66.3

[56] References Cited

U.S. PATENT DOCUMENTS

| 3,028,238 | 4/1962 | Puschel et al. | 96/100 |
| 3,227,554 | 1/1966 | Barr et al. | 96/100 |
| 3,620,745 | 11/1971 | Seymour | 96/74 |
| 4,088,491 | 5/1978 | Odenwalder et al. | 96/95 |

Primary Examiner—Richard C. Schilling
Attorney, Agent, or Firm—Connolly & Hutz

[57] ABSTRACT

Non-diffusible thioether compounds capable of releasing, on reaction with color developer oxidation compounds, a diffusible silver halide development inhibitor without at the same time forming permanent dyes to any substantial extent are characterized by containing a group of the formula

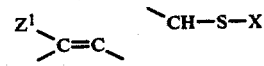

or its tautomeric form, wherein $Z^1$ represents an electron attracting substituent and X represents an aliphatic, aromatic or heterocyclic group that if released together with the sulfur atom, forms a diffusible silver halide development inhibiting mercaptane.

3 Claims, No Drawings

LIGHT SENSITIVE COLOR PHOTOGRAPHIC MATERIAL CONTAINING DEVELOPMENT INHIBITOR RELEASING COUPLER

This invention relates to a color photographic material which contains compounds which react with the oxidation products of color developer compounds to release development inhibiting substances.

The incorporation, in color photographic materials, of compounds which react with color developer oxidation products to release development inhibitors is already known. Compounds of this kind include, for example, the so-called DIR couplers (DIR=development inhibitor releasing) which have been described in U.S. Pat. No. 3,227,554. These compounds are color couplers which contain, in the coupling position, a thioether substituent which is split off in the color coupling reaction as a diffusible mercapto compound which has development inhibiting properties and is therefore capable of influencing the subsequent development of the silver halide.

These DIR couplers improve the properties of the color photographic materials in several respects. They allow the graininess, sharpness and gradation to be controlled, thereby substantially improving the color reproduction as a whole. Information on this subject may be found in the article entitled "Development Inhibitor Releasing" (DIR) Couplers in Colour Photography" in Photographic Science and Engineering 13, 74 (1969).

The DIR couplers mentioned above inevitably give rise to a dye together with the released development inhibitor. Careful choice of the DIR coupler employed is therefore necessary to ensure that the colors of a color photographic material will be well balanced. More particularly, one and the same DIR coupler must not be used in all the color forming layers of a multilayered color photographic material because the color of the dye formed from the coupler generally only corresponds to the color of the image dye in one of the layers while in the two other layers it would increase the unwanted side densities of the partial color images formed there.

These disadvantages do not occur if, instead of the DIR couplers, one uses compounds which release diffusible development inhibitors in their reaction with color developer oxidation products without at the same time forming a dye. Compounds of this kind, which may be referred to as DIR compounds to distinguish them from the DIR couplers mentioned above, have been described, for example, in U.S. Pat. No. 3,632,345. These compounds are mainly acetophenone derivatives which carry a thioether substituent in the ω-position. This substituent is obviously released in the reaction with oxidation products of color developer compounds. Another group of development inhibitor releasing compounds which also do not form dyes has been described in German Offenlegungsschrift No. 2,359,295. The DIR compounds in this case are cycloalkanones which carry a thioether substituent in the α-position to the keto group. Other DIR compounds have been described in German Offenlegungsschriften Nos. 2,362,752; 2,405,442; 2,448,063 and 2,529,350. It has however been found that, under certain operating conditions, the known DIR compounds are either too unstable or insufficiently reactive. In the former case, the development inhibitor is not released in imagewise distribution, so that there is a general loss in sensitivity, while in the latter case the inhibitor is released too slowly and is therefore not able to affect the development process to a sufficient extent.

It is an object of the present invention to find new compounds which react with color developer oxidation products to release development inhibiting substances without giving rise to permanent dyes during processing and which combine sufficient reactivity with sufficient stability.

A class of compounds has now been found which have an excellent DIR effect of the kind described above and which may be considered as belonging to the group of DIR compounds. These compounds contain a group represented by the following formula (I), which group may also exist in its tautomeric form (II).

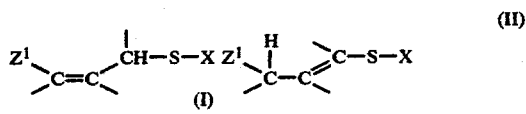

in which
$Z^1$ = represents an eletronattracting substituent and
$X$ = represents an aliphatic, aromatic or heterocyclic group which is split off together with the sulphur atom of the thioether link to form a diffusible mercapto compound which inhibits development of silver halide.

This invention relates to a color photographic material which contains a preferably non-diffusible thioether compound in at least one silver halide emulsion layer or in a light-insensitive layer of binder associated therewith, which thioether compound reacts with the oxidation product of a color developer substance containing a primary aromatic amino group to release a diffusible substance which inhibits the development of the silver halide.

The color photographic material contains a DIR compound having a group represented by the above formula. DIR compounds represented by the following formula III or its tautomers are preferred:

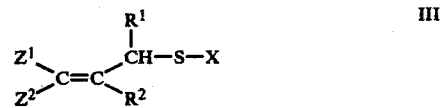

in which
$Z^1$ = represents a group which has an electronattracting effect, e.g. CN, $COR^3$, $SO_2R^3$,

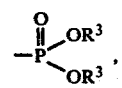

or a carbocyclic or heterocyclic aromatic group substituted by one of these groups;
$Z^2$ = represents hydrogen, alkyl, aryl, a heterocyclic group which is preferably attached through one of its carbon atoms, an alkoxy or alkylthio group, an amino group which may carry one or two alkyl substituents, including cyclic amino groups such as pyrrolidino, piperidino, or morpholino groups, or one of the groups mentioned for $Z^1$;

R¹ = represents one of the groups mentioned for Z², preferably hydrogen, or an alkyl, aryl, heterocyclic alkoxy or alkylthio group or a group of the formula:

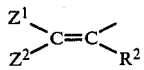

in which Z¹ and Z² have the meanings already specified and R² as defined below;

R² = represents one of the groups specified for Z², preferably hydrogen or alkyl, aryl or heterocyclic group, COR³ or CN;

R³ = represents hydroxyl, alkyl, aryl, a heterocyclic group, alkoxy or an amino group which may be monoalkyl or dialkyl substituted including a cyclic amino group.

The alkyl, alkoxy or alkylthio groups mentioned above may in particular contain up to 18 carbon atoms, and they may also be further substituted, for example, with halogen, hydroxyl, carboxyl, sulpho, aryl, a heterocyclic group, an amino group, carbamoyl or an acylamino group in which the acyl portion is derived from aliphatic or aromatic carboxylic or sulphonic acids, including carbamic acids or carbonic acid monoesters.

The carbocyclic aromatic groups and aryl groups mentioned above may be phenyl or naphthyl groups which may contain further substituents such as halogen, carboxyl, sulpho, aryl, a heterocyclic group, an amino group, carbamoyl or an acylamino group in which the acyl portion is derived from aliphatic or aromatic carboxylic or sulphonic acids, including carbamic acids or carbonic acid monoesters.

Suitable heterocyclic groups are in particular thienyl and furyl, which may also be further substituted.

The two groups R¹ and R² or Z¹ and Z² or R² and Z² may together constitute the ring members required to complete a preferably 5 or 6-membered carbocyclic or heterocyclic ring. A completed ring of this kind may contain other, condensed rings. Furthermore, the groups R¹, R² and Z² may combine to complete a multinuclear condensed ring system.

Examples of completed carbocylic rings are cyclohexane, tetraline, indane. Examples of completed heterocyclic rings are piperidine, dioxanedione and pyrazolone.

If Z¹ and Z² together complete a heterocyclic ring, this may for example, be a pyrazolone ring in which Z¹ and Z² together constitute a group represented by the following formula:

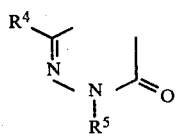

wherein R⁴ and R⁵ are substituent of the kind commonly found in the 1- and 3-positions of pyrazolinone color couplers; for example, R⁴ may represent an acylamino group and R⁵ may represent a phenyl group which may carry further substitutes such as alkoxy, aroxy, alkylthio or halogen.

X represents, as already indicated, an organic group which is split off together with the sulphur atom of the thioether link to form a diffusible mercapto compound which inhibits the development of the silver halide.

Examples of aliphatic groups which X may represent include

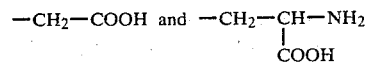

Examples of aromatic groups which X may represent include the following:

Tetrazolyl, such as 1-phenyltetrazolyl, 1-nitrophenyltetrazolyl, 1-naphthyltetrazolyl;

Triazolyl such as 1-phenyl-1,2,4-triazolyl;

Thiadiazolyl such as 2-phenylamino-1,3,4-thiadiazolyl;

Oxadiazolyl;

Thiazolyl, including benzothiazolyl and naphthiazolyl;

Oxazolyl, including benzoxazolyl and naphthoxazolyl, for example 7-sulphonaphtho-[2,3-d]oxazolyl;

Pyrimidyl such as 4-methyl-6-aminopyrimidyl or 4-methyl-6-hydroxypyrimidyl, or

Triazinyl such as thiadiazolotriazinyl.

One of the groups Z¹, Z², R¹ and R² or a ring completed by two of these groups preferably contains a group which confers diffusion resistance, preferably a long chain alkyl group. Groups are regarded as conferring diffusion resistance if they allow the compounds according to the invention to be incorporated in a diffusion-fast form in the hydrohilic colloids normally used in photographic materials. Groups which are particularly suitable for this purpose are organic groups which generally contain straight or branched chain aliphatic groups and which may also contain carbocylic or heterocyclic aromatic groups. The aliphatic portion of these groups generally contains from 8 to 20 carbon atoms. The groups are attached to the remainder of the molecular either directly or indirectly, e.g. through one of the following groups: —CONH—; —SO₂NH—; —CO—; —SO₂—; —NR— in which R represents hydrogen or alkyl; —O— or —S—.

In addition, the group which confers diffusion resistance may also contain groups which confer solubility in water, e.g. sulpho or carboxyl groups, and these may also be present in their anionic form. Since the diffusion properties depend on the size of the molecule of the compound as a whole, it is in some cases sufficient, for example, if the molecule as a whole is large enough, to use short chain groups for conferring diffusion resistance.

The following are examples of thioether compounds represented by the general formula III:

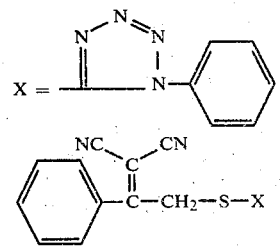

1.

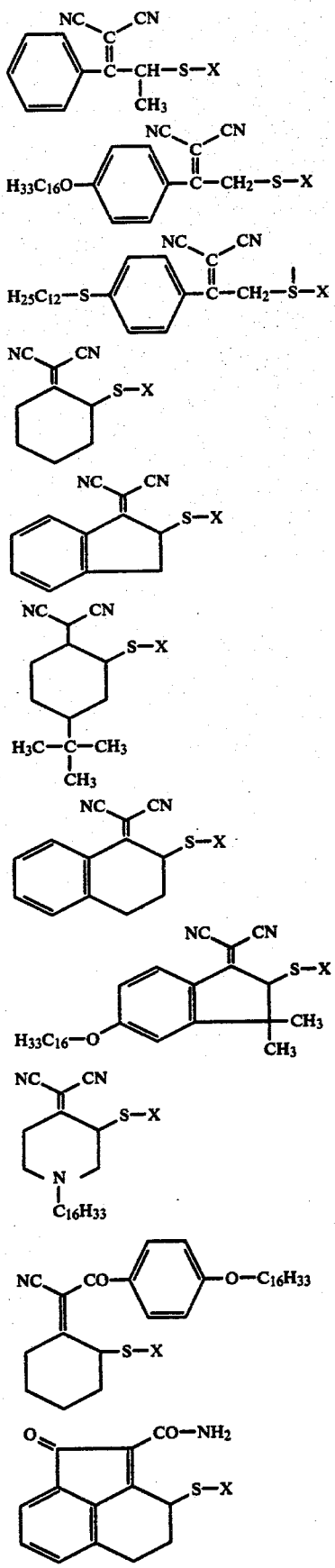

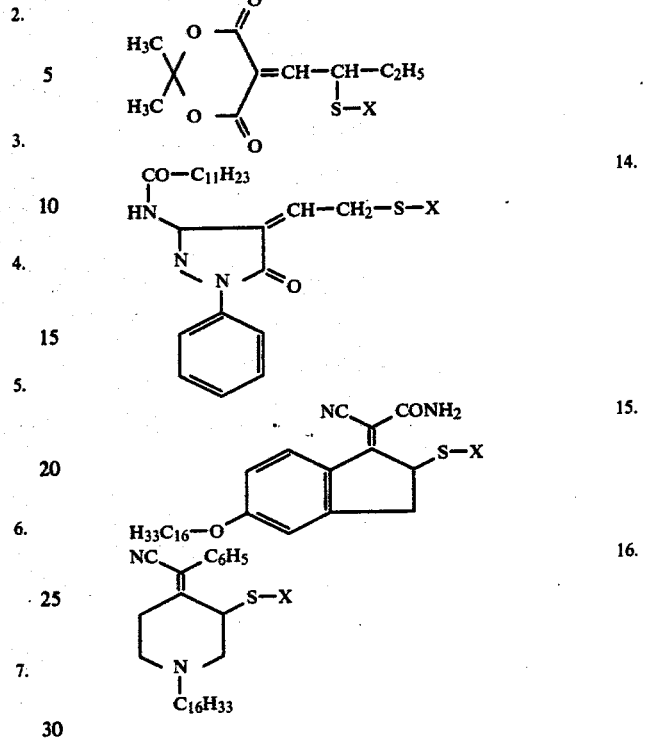

The compounds required as starting materials for synthesising the DIR compounds used in accordance with the invention can be prepared by known methods, for example as described in Organic Reactions, Vol. 15, pages 204–605, John Wiley & Sons, Inc. and Formation of C-C-Bonds, Vol. II, pages 508–639, G. Thieme Verlag, Stuttgart, 1975.

Introduction of the inhibitor group —S—X may be carried out by known methods, e.g. as described in U.S. Pat. No. 3,632,345, or by the method commonly used for ketones and pyrazolones, i.e. by halogenating the ylidene compound in the allyl position and then reacting with the XSH compound, preferably in the presence of bases which convert the XSH compound into its salt, or by directly reacting with the salt of the XSH compound or by reacting the non-halogenated ylidene compound with the sulphenyl halide X—S—Hal, preferably in the presence of a base, or with the disulphide X—S—S—X, if desired in the presence of a base. Alternatively, the compounds according to the invention may be obtained by the condensation of a keto compound which already contains the group —S—X with a methylene active compound $Z^1$—$CH_2$—$Z^2$.

EXAMPLES OF PREPARATION

Compound 2

1st Stage:

2.7 ml of bromine are added to 9.1 g of 1-phenyl-propylidene-propanedinitrile and 0.2 g of acetophenone in 100 ml of benzene and the mixture is stirred at room temperature for 1.5 hours. The residue obtained after evaporation under vacuum is recrystallised from 25 ml of ethanol. 11,7 g of 2-bromo-1-phenyl-propylidene-propanedinitrile melting at 103° to 104° C. are obtained.

2nd Stage:

4 g of 1-phenyl-5-tetrazolyl sodium mercaptide and 5.2 g of the intermediate product from Stage 1 in 40 ml of acetone are stirred together at room temperature overnight. The precipitate obtained by the addition of water is dissolved in 20 ml of chloroform. 80 ml of methanol are added, and the precipitate thereby obtained is stirred up with 40 ml of methanol and suction filtered. 4.9 g of 1-phenyl-2-(1-phenyl-5-tetrazolylthio)-propylidenepropanedinitrile melting at 145° to 146° C. are obtained.

COMPOUND 4

1st Stage:

32 g of 1-(4-dodecylthiophenyl)-1-ethanone, 6.6 g of malodinitrile, 3 ml of glacial acetic acid and 1,3 ml of n-hexylamine in 200 ml of cyclohexane are heated under reflux for 4 hours, using a water separator. The solution is evaporated under vacuum, the residue is stirred up with 100 ml of methanol and the precipitate obtained is suction filtered. 26.5 g of 1-(4-dodecylthiophenyl)-ethylidenepropanedinitrile melting at 47° to 48° C. are obtained.

2nd Stage:

18.5 g of the intermediate compound obtained in Stage 1, 17.5 g of di-(1-phenyl-5-tetrazolyl)-disulphide and 4.1 g of sodium acetate sicc. in 200 ml of acetonitrile are stirred together at 50° C. for 45 minutes. After cooling and the addition of 200 ml of methanol, the precipitate is suction filtered and recrystallised from ethanol. 8.4 g of 1-(4-dodecylthiophenyl)-2-(1-phenyl-5-tetrazolylthio)-ethylidene propanedinitrile melting at 100° to 101° C. are obtained.

Compound 9

1st Stage:

3,3-Dimethyl-5-cetyloxy-1-indanylidene-propanedinitrile melting at 89.5° to 90.5° C. are obtained by a method similar to that used for Stage 1 of the preparation of Compound 4.

2nd Stage:

3,3-Dimethyl-5-cetyloxy-2-(1-phenyl-5-tetrazolylthio)-1-indanylidene-propanedinitrile melting at 100°–102° C. is obtained by a method similar to that used in Stage 2 of the preparation of Compound 4.

The compounds according to the invention are comparable to the known DIR couplers disclosed in U.S. Pat. No. 3,227,554 in that they are also non-diffusible thioether compounds which react with color developer oxidation products to release a diffusible mercaptan which inhibits the development of the silver halide. However, they differ from the known DIR couplers in that, when they react with oxidation products of the developer substances, they generally do not give rise to colored reaction products which would impair the colour image finally obtained. The compounds according to the invention may therefore be described as DIR compounds, in contrast to the known DIR couplers. According to U.S. Pat. No. 3,148,062, DIR couplers are subdivided into those in which the releasable group already has an inhibitory effect before coupling takes place and those in which the inhibitory effect arises only when the molecular group is released from the coupling position. In the latter case, the inhibitor is said to be non-preformed. According to this terminology, the compounds according to the invention should therefore be described as non-diffusible compounds which react with color developer oxidation products to release a diffusible, non-preformed development inhibitor.

The compounds according to the invention are more highly reactive than the compounds according to U.S. Pat. No. 3,632,345 and German Offenlegungsschrift No. 2,359,295. This is particularly advantageous when development is carried out at a relatively low pH, e.g. at pH 10 to 11. The DIR compounds according to the invention are still sufficiently active under these conditions.

The DIR compounds according to the invention are particularly suitable for use in those color photographic multilayer materials in which the silver halide which is exposed imagewise is subsequently developed by the usual color developers, e.g. the usual aromatic compounds based on p-phenylene diamine which contain at least one primary amino group. The following are examples of suitable color developers:

N,N-dimethyl-p-phenylenediamine;
N,N-diethyl-p-phenylenediamine;
Monomethyl-p-phenylenediamine;
2-Amino-5-diethylaminotoluene;
N-butyl-N-ω-sulphobutyl-p-phenylenediamine;
2-amino-5-(N-ethyl-N-β-methanesulphonamidoethyl-amino)-toluene;
N-ethyl-N-β-hydroxyethyl-p-phenylenediamine;
N,N-bis-(β-hydroxyethyl)-p-phenylenediamine;
2-Amino-5-(N-ethyl-N-β-hydroxyethylamino)-toluene, and the like.

Other suitable color developers have been described, for example, in J. Amer. Chem. Soc. 73, 3100 (1951).

The developer compounds are generally introduced into an alkaline development both used for treating the color photographic material which has been exposed imagewise, but they may also be incorporated in one or more layers of the photographic material. In the latter case, the developer compounds contain groups which confer diffusion resistance and they are incorporated in a layer which also contains a diffusion resistant color coupler or a diffusion resistant color providing compound as described, for example, in U.S. Pat. No. 3,705,035. Development then only requires an alkaline activator solution which contains an auxiliary developer, for example phenidone. The oxidation product of color developer produced on development reacts with the non-diffusible color coupler to form a non-diffusible image dye or it reacts with the non-diffusible color providing compound to form an imagewise distribution of diffusible dyes which can be transferred to an image receptor layer. At the same time, the oxidation product of the color developer reacts with the non-diffusible DIR compounds according to the invention, which are present at the same time, this reaction resulting in the release of diffusible inhibitor molecules without the formation of a permanent dye from the remainder of the molecule of DIR compound.

The color photographic multilayered material according to the invention contains a DIR compound in at least one of its layers. This compound may be incorporated in one of the light-sensitive silver halide emulsion layers or in a hydrophilic layer of binder which is associated with such a light-sensitive silver halide emulsion layer but need not itself be light-sensitive. By "associated" is meant in this context a layer which is situated in such a spatial relationship to the light sensitive silver halide emulsion layer that significant quantities of color developer oxidation products diffuse into it from the light sensitive silver halide emulsion layer, when development takes place in the silver halide emulsion layer. The concentration of DIR compound according to the invention in the layer in which it is incorporated may vary within wide limits, e.g. between $1 \times 10^{-3}$ and $300\times10^{-3}$ mol per kg of silver halide in the case of the silver halide emulsion layer while, in the associated layer of binder, it may vary e.g. between $0.05\times10^{-3}$ and $1\times10^{-3}$ mol per gram of binder. The concentration depends in each case on the purpose for which the DIR compound is used, the silver halide emulsion, and whether the DIR compound is incorporated in a silver halide emulsion layer or in a light-insensitive layer of binder. The upper limit generally lies at the concentrations at which color couplers are also used in photographic layers but it is not essential to observe such a limit since the DIR compounds according to the invention do not contribute to the color image.

The color developer oxidation products react with the compounds according to the invention to form colorless products and are thereby prevented from taking part in any color-producing reactions. The compounds according to the invention are therefore comparable in this respect to the known white couplers such as those described in U.S. Pat. No. 2,998,314. At the same time, this reaction between the color developer oxidation products and the compounds according to the invention also releases a diffusible mercapto compound which is capable of inhibiting any further development of the silver halide. This inhibitory action can occur both in the layer which contains the compounds according to the invention, if this layer contains developable silver halide, and in adjacent silver halide emulsion layers into which the released inhibitor is capable of diffusing. In this way, the compounds according to the invention can be used for controlling development in various ways in each of the light-sensitive silver halide emulsion layers, and development in one silver halide emulsion layer can be influenced by the result of imagewise development in another layer due to the vicinal effects which can be produced by the compounds according to the invention, so that an overall improvement in the graininess, sharpness and colour reproduction can be achieved.

The light sensitive silver halide emulsion layers of the photographic material according to the invention differ from each other in their spectral sensitivities and each of them has associated with it at least one non-diffusible compound for producing an image dye of a color which is generally complementary to the spectral sensitivity. These compounds may be conventional color couplers which are generally incorporated in the silver halide layers. Thus, the red sensitive layer, for example, contains a non-diffusible color coupler for producing the cyan partial color image, generally a coupler based on phenol or α-naphthol. The green sensitive layer contains at least one non-diffusible color coupler for producing the magenta partial color image, usually a colour coupler based on 5-pyrazolene or indazolene. The blue sensitive layer unit contains at least one non-diffusible color coupler for producing the yellow partial color image, generally a color coupler containing an open chain ketomethylene group. Larger number of color couplers of these kinds are known and have been described in numerous Patent Specifications as well as in other publications, for example in "Farbkuppler" by W. Pelz in "Mitteilungen aus den Forschungslaboratorien der Agfa, Leverkusen/Munchen", Volume III (1961) page 111. The non-diffusible color couplers may contain a releasable substituent in the coupling position so that they require only two equivalents of silver halide to produce color, in contrast to the usual four equivalent couplers. The color couplers used are generally themselves colourless but, if the releasable substituent contains a chromophoric group, as in the case of the known masking couplers, the color couplers generally have a color which is suitable for masking unwanted side densitites of the image dye by conventional masking techniques. The image dyes produced from the color couplers are generally resistant to diffusion.

If one or more of the silver halide emulsion layers in the material according to the invention is a double layer consisting of two partial layers which may differ from each other in their sensitivity or in their silver/coupler ratio, as has been proposed for achieving an improved relationship of sensitivity to graininess, i.e. for increasing the sensitivity without coarsening the color grain (e.g. German Pat. No. 1,12,470; U.S. Pat. No. 3,726,681; German Offenlegungsschriften Nos. 2,322,165 and 2,416,982), one or both of these partial layers of a double layer may contain one or more of the DIR compounds according to the invention.

If desired, the image dyes may first be produced in a diffusible form and fixed only later, after they have been transferred to an image receiving layer. This method is knwon from various dye diffusion transfer processes, e.g. those described in U.S. Pat. Nos. 3,227,550 and 3,628,952 and German Pat. No. 1,772,929. In such cases, colored or colorless non-diffusible color providing compounds which release diffusible dyes in imagewise distribution when development takes place are associated with the light-sensitive silver halide emulsions. These color providing compounds are incorporated either in the silver halide emulsion layer or in an associated hydrophilic layer of binder which may contain development nuclei, for example, and may also contain a silver halide which is developable without exposure.

When conventional silver halide emulsions are used in combination with non-diffusible color couplers or with non-diffusible color providing compounds, negative color images are normally obtained. However, both the DIR compounds according to the invention and DIR couplers may advantageously be used in reversal processes which give rise to positive images. These processes may be any of the usual reversal processes in which the photographic material is subjected to a black-and-white development after it has been exposed imagewise, and is subsequently color developed after a diffuse second exposure, as well as reversal processes in which the imagewise information in the photographic material is reversed due to the presence of the DIR compounds according to the invention. This reversal can take place if, for example, a silver halide emulsion layer which is capable of spontaneous development, i.e. without previous exposure, and which contains a color coupler or color providing compound is arranged adjacent to a conventional silver halide emulsion layer which contains a DIR compound. It is obvious that the DIR couplers or DIR compounds used for such a procedure must be capable of rapidly releasing the inhibitor so that it can inhibit development imagewise in the spontaneously developable layer.

The non-diffusible color couplers and color providing compounds as well as the non-diffusible, development inhibitor releasing compounds used according to the invention are added to the light-sensitive silver halide emulsions or other casting solutions by the usual, known methods. If the compounds are soluble in water or alkalies, they may be added to the emulsions in the form of aqueous solutions, if desired with the addition of water-miscible organic solvents such as ethanol, acetone or dimethylformamide. If the non-diffusible color couplers, color providing compounds and development inhibitor releasing compounds used are insoluble in water or alkalies, they may be emulsified in known manner, for example by mixing a solution of these compounds in a low boiling organic solvent either directly with the silver halide emulsion or first with an aqueous gelatine solution and then evaporating off the organic solvent. The resulting emulsion of the given compound in gelatine is then mixed with the silver halide emulsion. If desired, so-called coupler solvents or oil formers may also be added when emulsifying such hydrophobic compounds. These coupler solvents or oil formers are generally higher boiling organic compounds in which the non-diffusible color couplers or development inhibitor releasing compounds which are required to be emulsified in the silver halide emulsions become occluded in the form of oily droplets. Information on this may be found, for example, in U.S. Pat. Nos. 2,322,027; 3,689,271; 3,764,336 and 3,765,897. If the compounds according to the invention are emulsified in the layers with the aid of such oil formers, the groups which confer diffusion resistance in the compounds according to the invention need not be so powerful in their effect, i.e. in this case even shorter alkyl groups such as isoamyl groups may be sufficient to prevent diffusion of the compounds according to the invention in the layers of photographic material.

Furthermore, the DIR compounds according to the invention may be prepared as aqueous dispersions and added in this form to the casting solutions. In that case, aqueous suspensions of the compounds are finely milled, for example by vigourous stirring with the addition of sharp sand and/or by the application of ultra sound, optionally in the presence of a suitable hydrophilic binder such as gelatine.

The usual silver halide emulsions may be used for the present invention. The silver halide contained in them may be silver chloride, silver bromide or mixtures thereof, which may have a small silver iodide content of up to 10 mol %. Both conventional negative emulsions and direct positive emulsions may be used, e.g. those which have a high sensitivity in the interior of the silver halide grains, for example the emulsions described in U.S. Pat. No. 2,592,250.

The binder used for the photographic layers is preferably gelatine but this may be partly or completely replaced by other natural or synthetic binders. Suitable natural binders include, for example, alginic acid and its derivatives, such as its salts, esters or amides, cellulose derivatives such as carboxymethylcellulose, alkylcelluloses such as hydroxyethylcellulose, starch or its derivatives such as its ethers or esters, or carrageenates. Suitable synthetic binders include polyvinyl alcohol, partially saponified polyvinyl acetate and polyvinyl pyrrolidone.

The emulsions may also be chemically sensitized, e.g. by the addition of sulphur compounds such as allyl isothiocyanate, allylthiourea or sodium thiosulphate at the chemical ripening stage. Reducing agents may also be used as chemical sensitizers, e.g. the tin compounds described in Belgian Pat. No. 493,464 or No. 568,687, or polyamines such as diethylene triamine or aminomethane sulphinic acid derivatives, e.g. as described in Belgian Pat. No. 547,323.

Noble metals such as gold, platinum, palladium, iridium, ruthenium or rhodium and compounds of these metals are also suitable chemical sensitizers. This method of chemical sensitization has been described in the article by R. Koslowsky, Z. Wiss. Phot. 46, 65 to 72 (1951).

The emulsions may also be sensitized with polyalkylene oxide derivatives, e.g. with a polyethylene oxide having a molecular weight of between 1000 and 20,000, or with condensation products of alkylene oxides and aliphatic alcohols, glycols, cyclic dehydration products of hexitols, alkyl substituted phenols, aliphatic carboxylic acids, aliphatic amines, aliphatic diames or amides. The condensation products have a molecular weight of at least 700, preferably more than 1000. These sensitizers may, of course, be combined in order to produce special effects, as has been described in Belgian Pat. No. 537,278 and British Pat. No. 727,982.

The emulsions may also be spectrally sensitized, e.g. with the usual monomethine or polymethine dyes such as acid or basic cyanines, hemicyanines, streptocyanines, merocyanines, oxonoles, hemioxonoles, styryl dyes or others, including also trinuclear or higher nuclear methine dyes, for example rhodacyanines or neocyanines. Sensitizers of this kind have been described, for example in the work by F. M. Hamer "The Cyanine Dyes and Related Compounds" (1964), Interscience Publishers John Wiley and Sons.

The emulsions may contain the usual stabilizers, e.g. homopolar compounds or salts of mercury which have aromatic or heterocyclic rings, such as mercaptotriazoles, or simple mercury salts, sulphonium mercury double salts and other mercury compounds. Azaindenes are also suitable stabilizers, particularly tetra- or penta-azaindenes, especially those which are substituted with hydroxyl or amino groups. Compounds of this kind have been described in the article by Birr, Z. Wiss. Phot. 47, 2 to 27 (1952). Other suitable stabilizers include heterocyclic mercapto compounds, e.g. phenylmercaptotetrazole, quaternary benzothiazole derivatatives and benzotriazole.

The emulsions may be hardened in the usual manner, for example with formaldehyde or halogenated aldehydes which contain a carboxyl group, such as mucobromic acid, diketones, methanesulphonic acid esters, dialdehydes or vinyl sulphone compounds.

The photographic layers may also be hardened with epoxy hardeners, heterocyclic ethyleneimine hardeners or acryloyl hardeners. Examples of such hardeners have been described in German Offenlegungsschrift No. 2,263,602 and in British Pat. No. 1,266,655, among others. The layers may also be hardened by the process according to German Offenlegungsschrift No. 2,218,009 in order to produce colour photographic materials which are suitable for high temperature processing.

EXAMPLE

Arrangement of the light-sensitive color photographic material

The DIR compounds are preferably used in multilayer materials such as those used, for example, for the preparation of negative or positive light-sensitive color photographic materials.

The effectiveness of the DIR compounds according to the invention is illustrated by the example of a typical arrangement of layers or partial layers for color negative materials.

Light-sensitive photographic material:

Arrangement of layers

Support: Substrated cellulose triacetate support.
(a) Intermediate layer of gelatine (1μ);
(b) Cyan layer consisting of a silver halide emulsion sensitized to the red spectral region and a colour coupler for cyan (silver application: 4 g of silver/m²);
(c) Intermediate layer of gelatine (1μ);
(d) Magenta layer consisting of a silver halide emulsion sensitized to the green spectral region and a color coupler for magenta (silver application: 3.5 g of silver/m²);
(e) Intermediate layer of gelatine (1μ);
(f) Yellow filter layer (2μ);
(g) Yellow layer consisting of a silver halide emulsion which is sensitive to the blue spectral region and a color coupler for yellow (silver application: 1.5 g of silver/m²);
(h) Protective layer of gelatine (1μ).

The material is hardened with a sulphobetainecarbodiimide represented by the following formula $$CH_3-N=C=N-(CH_2)_3-\overset{\oplus}{\underset{|}{N}}(CH_3)_2$$
$$(CH_2)_4-SO_3^{\ominus}$$

(described in DT-OS-2 439 553; compound 1). The individual red-(b) green-(b) and blue-(g) sensitive partial layers are prepared by casting the following solutions.

(b) 1 kg of a red-sensitized silver halide emulsion (100 g of silver/kg of emulsion) in which the silver halide consists of 95 mol % of silver bromide and 5 mol % of silver iodide, 50 ml of a 1% solution in methanol of 1,3,3a,7-tetraaza-4-hydroxy-6-methyl-indene, 360 g of a coupler dispersion of a solution of 15 g of the cyan coupler represented by the following formula:

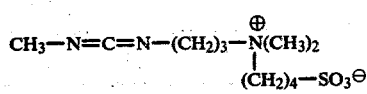

in
7.5 g of dibutylphthalate,
30 g of diethylcarbonate
100 ml of a 4% aqueous gelatine solution
0.8 g of a wetting agent, e.g. a sulphonated paraffin hydrocarbon,
10 ml of a 10% aqueous saponin solution and 1000 ml of water.

(d) The composition of the casting solution used for the green sensitive layer is similar to that of the red sensitive layer (b) except that the emulsion is sensitized to the green region of the spectrum and instead of the cyan coupler dispersion it contains 192 g of a dispersion of the magenta coupler represented by the following formula:

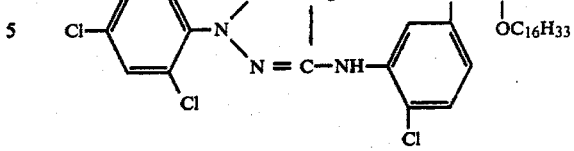

in a composition similar to that used for the cyan emulsion in layer (b).

(g) The composition of the casting solution for the blue sensitive layer is similar to that of the red sensitive layer (b) except that the emulsion is sensitized only to the blue region of the spectrum and instead of cyan coupler dispersion it contains 175 g of a 5% solution of the yellow coupler represented by the following formula:

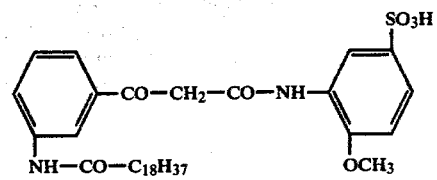

in an aqueous 8% gelatine solution.

Gelatine layers a,c,e and h are prepared by casting the following solution:
125 ml of a 10% gelatine solution,
500 ml of water,
5 ml of a 10% aqueous solution of saponin.

The casting solution for the yellow filter layer is identical to the casting solution for gelatine layers a,c,e and h except for the addition of 1.4 g of finely dispersed metallic silver of the kind generally used as barrier filter for the blue spectral portion of light.

Processing

The material is exposed to blue, green and red light in a conventional sensitometer behind a grey step wedge and the appropriate colour separation filters. It is then developed in a color developer having the following composition:
2 g of the sodium salt of isopropanoldiaminotetracetic acid
20 g of potassium carbonate
4 g of potassium sulphite
1.5 g of potassium bromide
2 g of hydroxylamine
5 g of color developer represented by the following formula

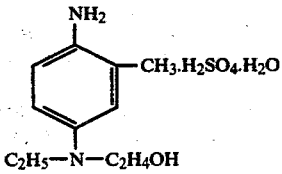

made up to 1 liter; ph adjusted to 10.2. Development: 3¼ minutes at 38° C.

The subsequent steps of the process indicated below each take 3¼ minutes. The bath temperature used is also 38° C. in each case.

Short stop bath:
  30 ml of acetic acid (concentrated)
  20 g of sodium acetate
  water up to 1 liter
Washing
Bleaching bath:
  100 g of potassium ferricyanide
  15 g of potassium bromide
  water up to 1 liter
Washing
Fixing bath: 20% aqueous solution of sodium thiosulphate
Final washing
Assessment of the exposed and developed samples:

Since the arrangement of layers prepared for the experiments were not masked, the side densities of the dyes produced interfere with the determination of the true IIE (Interimage effect). To eliminate the error due to side densities, gradation curves are drawn up from the analytical densities obtained by converting the measured integral densities. The γ-values are read off these analytical color density curves and used to calculate the IIE values. The IIE is defined as follows:

$$IIE = \frac{\gamma s - \gamma w}{0.6} \cdot 100\%$$

where
  s represents selective exposure
  w represents white exposure.

The graininess is given in $\tau_D$-values (rms values obtained with a shutter diameter of 29μ) by the method described by H. T. Buschman in "Bestimmung der Kornigkeit photographischer Schichten mit Hilfe digitaler Technik" in OPTIK 38, 1973, pages 169–219.

The emulsifiable DIR compounds are emulsified by the following method:

A solution of 10 g of DIR compound in 10 g of dibutylphthalate, 30 ml of ethyl acetate and 5 g of dimethylformamide is emulsified in a solution of 100 ml of a 5% aqueous gelatine solution and 0.8 g of a wetting agent, e.g. sulphonated paraffin hydrocarbons, by means of vigorous mixing in a mixing siren. Method of using the DIR compounds:

EXAMPLE 1

Incorporation of the DIR compound in red sensitive layer b:
  Arrangement of layers: consisting of layers, a, b, and c.
  Sample 1: No DIR compound in layer b.
  Sample 2: The emulsion of DIR compound 4 is added to the casting solution for layer b in an amount of 50 g of 1 kg of emulsion.
  Sample 3: DIR compound 3 is added to the casting solution for layer b in an amount of 50 g to 1 kg of emulsion.

The samples were exposed to red light behind a step wedge and developed as described above. The DIR compounds cause flattening of the gradation due to their inhibitory action.

Table 1

| Sample | γ | Graininess $\sigma_D \cdot 10^{31\ 2}+)$ |
|---|---|---|
| 1 | 1.50 | 2.65 |
| 2 | 0.95 | 1.95 |

Table 1-continued

| Sample | γ | Graininess $\sigma_D \cdot 10^{31\ 2}+)$ |
|---|---|---|
| 3 | 1.05 | 2.05 |

*) at density D = 1 and γ = 1.00

If the layers are cast to thicknesses such that all three samples have a gradation of 1.00, the graininess of the samples containing the DIR compound is distinctly lower than in Sample 1 for virtually the same sensitivity (Table 1).

EXAMPLE 2

Incorporation of the DIR compound in the yellow filter layer of the arrangement of layers indicated above:

To the filter yellow layer with colloidal silver used for producing a yellow density of 0.8 density units there was added an emulsion of DIR compound 9 in the quantity corresponding to 0.20 g of DIR compound per square meter. When the magenta gradations obtained on exposure to green light were compared with those obtained on exposure to white light, an increase in the magenta IIE was found with the filter yellow layer which contained the DIR compound:

| Sample | DIR compound in yellow filter layer | IIE % PP | Exposure Green PPγ_s | White PPγ_w |
|---|---|---|---|---|
| 1 | DIR compound 9 | 42 | 1.05 | 0.80 |
| 2 | — | 18 | 1.10 | 0.90 |

PP = magenta

EXAMPLE 3

Incorporation of DIR compound 4 in cyan layer b and of DIR compound 3 in magenta layer d:

The emulsion of DIR compound 3 is added to the casting solution of layer d in the amount corresponding to 60 g to 1 kg of silver halide emulsion. The emulsion of DIR compound 4 is added to the casting solution of layer b in an amount corresponding to 30 g per 1 kg of silver halide emulsion. Another sample containing no DIR compound in layer b was prepared for comparison.

The samples were exposed to green and white light behind a step wedge and developed as described above. The effect of the DIR compound contained in the cyan layer on the magenta IIE was investigated:

| Sample | DIR compound | IIE % PP | Exposure Green PPγ_s | White PPγ_w |
|---|---|---|---|---|
| 1 | 4 in b 3 in d | 30 | 0.89 | 0.71 |
| 2 | none in b 3 in d | 15 | 0.90 | 0.81 |

We claim:
1. A color photographic recording material comprising at least one light sensitive silver halide emulsion layer and containing in said light sensitive silver halide emulsion layer or in a light-insensitive binder layer associated thereto, a non-diffusible thioether compound capable of reacting with the oxidation product of a color developer compound containing a primary aromatic amino group, to release a diffusible substance which inhibits development of the silver halide, said non-diffusible thioether compound being a compound corresponding to the following formula or the corresponding tautomeric form:

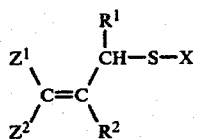

wherein
X = an aliphatic group, an aromatic group or a heterocyclic group which on reaction with the color developer oxidation product, is released together with the sulfur atom of the thioether link to form a diffusible mercapto compound which inhibits the development of the silver halide;
$Z^1$ = an electron attracting group selected from the group consisting of CN, $COR^3$ and $SO_2R^3$ where $R^3$ represents hydroxyl, alkyl, aryl, a heterocyclic group, alkoxy or amino, $Z^2$, $R^1$ and $R^2$ represent hydrogen, alkyl, aryl, a heterocyclic group, alkoxy, alkylthio groups or groups as defined under $Z^1$, or
$R^1$ and $R^2$ together, $Z^1$ and $Z^2$ together or $Z^2$ and $R^2$ together represent the ring members required for completing a 5-membered or 6-membered carbocyclic or heterocyclic ring.

2. Material as claimed in 1, in which $R^1$ represents hydrogen, alkyl a heterocyclic group, alkoxy or alkylthio.

3. Material as claimed in claim 1, in which $Z^1$ and $Z^2$ together represent a group of the following formula:

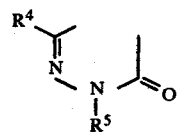

wherein $R^4$ represents an acylamino group and $R^5$ represents a phenyl group which may carry further alkoxy, aroxy, alkylthio or halogen substituents.

* * * * *

UNITED STATES PATENT OFFICE
CERTIFICATE OF CORRECTION

Patent No. 4,186,012　　　　　　　Dated January 29, 1980

Inventor(s) Heinrich Odenwalder et al

It is certified that error appears in the above-identified patent and that said Letters Patent are hereby corrected as shown below:

In the Abstract, the formula should read as follows:

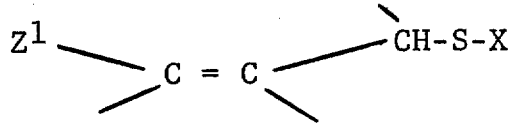

Column 15, line 32 should read --
　"The graininess is given in $\sigma_D$-values ... "

Column 15, line 65 should read --

| Sample | $\gamma$ | Graininess $\sigma_D \cdot 10^{-2}+$) |
|---|---|---|

Signed and Sealed this

*Seventh* Day of *October 1980*

[SEAL]

*Attest:*

SIDNEY A. DIAMOND

*Attesting Officer*　　*Commissioner of Patents and Trademarks*